United States Patent
Lyman

(10) Patent No.: US 8,151,655 B2
(45) Date of Patent: Apr. 10, 2012

(54) CROSS-BELT SAMPLER FOR MATERIALS CONVEYED ON A BELT CONVEYOR

(76) Inventor: Geoffrey John Lyman, Bellbowrie (AU)

( * ) Notice: Subject to any disclaimer, the term of this patent is extended or adjusted under 35 U.S.C. 154(b) by 731 days.

(21) Appl. No.: 12/305,719

(22) PCT Filed: Jun. 18, 2007

(86) PCT No.: PCT/AU2007/000847
§ 371 (c)(1),
(2), (4) Date: Dec. 19, 2008

(87) PCT Pub. No.: WO2007/147201
PCT Pub. Date: Dec. 27, 2007

(65) Prior Publication Data
US 2009/0205446 A1    Aug. 20, 2009

(30) Foreign Application Priority Data
Jun. 19, 2006  (AU) .................. 2006903304

(51) Int. Cl.
*G01N 1/20* (2006.01)
*G01N 1/08* (2006.01)

(52) U.S. Cl. ............... 73/863.91; 73/863.53; 73/863.56
(58) Field of Classification Search .. 73/863.52–863.53, 73/863.55–863.56, 863.91–863.92
See application file for complete search history.

(56) References Cited

U.S. PATENT DOCUMENTS

| | | | | |
|---|---|---|---|---|
| 3,181,369 A | * | 5/1965 | Taylor | 73/863.91 |
| 4,133,210 A | * | 1/1979 | Jaeger | 73/863.91 X |
| 4,558,602 A | * | 12/1985 | Redding | 73/863.53 |
| 4,641,540 A | | 2/1987 | Ellis | |
| 4,955,242 A | * | 9/1990 | Long | 73/863.91 |
| 5,115,688 A | | 5/1992 | van der Merwe et al. | |
| 5,392,659 A | | 2/1995 | Ford, Jr. et al. | |
| 5,767,421 A | | 6/1998 | Long et al. | |
| 2002/0000131 A1 | | 1/2002 | Long et al. | |

FOREIGN PATENT DOCUMENTS

AU    2006903304    *    6/2006

OTHER PUBLICATIONS

International Search Report for PCT/AU2007/000847 mailed Aug. 13, 2007, 3 pages.

* cited by examiner

*Primary Examiner* — Thomas P Noland
(74) *Attorney, Agent, or Firm* — Panitch Schwarze Belisario & Nadel LLP

(57) ABSTRACT

A cross-belt sampler (100) for material (70) on a belt-conveyor (60) has a cutter head (50), where the cutting edges (9) of the side plates (3,4) lie on lines co-incident with the axis of rotation (1) of the cutter head (50). The rear plate (5) lies on a plane parallel to the axis of rotation (1) and a truncated plate (6) eliminates a sharp corner in which the material (70) may be compacted. The axis of rotation (1) of the cutter head (50) is offset a distance (28) relative to the longitudinal axis of the belt conveyor (60).

17 Claims, 12 Drawing Sheets

US 8,151,655 B2

CROSS-BELT SAMPLER FOR MATERIALS CONVEYED ON A BELT CONVEYOR

CROSS-REFERENCE TO RELATED APPLICATION

This application is a Section 371 of International Application No. PCT/AU2007/000847, filed Jun. 18, 2007, which was published in the English language on Dec. 27, 2007 under International Publication No. WO 2007/147201 A1, and the disclosure of which is incorporated herein by reference.

BACKGROUND OF THE INVENTION

1. Field of the Invention

The device described herein is a new design for a sampler head or sample cutter for the extraction of representative sample increments from a material stream conveyed on a belt conveyor. The sampler is of a type generally called a cross-belt sampler, but is also known as a go-belt sampler or a hammer sampler.

The new design corrects the technical faults that are present in the known designs. The novel design principle for the sample cutter geometry can in fact be used to show that all the known designs for cross-belt sampler cutters, with one exception, take a sample that is not representative of the material on the belt.

2. Prior Art

Sampling of bulk materials conveyed on a conveyor belt is a critical operation in the transfer of bulk commodities between buyer and seller or within industrial processing operations. It is usual to sample the commodity as it is loaded onto transport (road, rail or ship) and to sample it as it is off-loaded at the buyer's site or at the boundaries of the processing operation. The sample that is analysed to estimate the quality or value of the shipment must be representative of the entire shipment. A sample is said to be representative of the material sampled when the expected assay of the sample is equal to the true mean assay of the lot of material being sampled. Modern statistical sampling theory provides a means of determining how many sample increments and the total mass of material that must be extracted from the flow of material as it is loaded or off-loaded in order to ensure that the expected value of the absolute difference between the properties of the accumulated sample and the true properties of the entire shipment is limited to an acceptable magnitude. The increments extracted from the stream are combined into the representative sample and that sample may be further sub-sampled by other devices to arrive at the final mass of material submitted for physical and chemical analysis. If all the sampling equipment used in taking and processing the sample increments and the final sample is correctly designed, any difference between the properties of the accumulated sample and the true properties of the entire shipment will be randomly distributed with some variance and a statistical expected value of zero. When the statistical expected value of this difference is zero, the sampling equipment is said to be unbiased. Lack of bias in commercial sampling of commodities is usually a contractual requirement and it is essentially mandatory that sampling equipment be unbiased.

The demonstration that a sampling device is unbiased is accomplished in two stages. First, an analysis of its geometry and motion through the stream of material to be sampled must show that, at an arbitrary position in the stream, the time interval during which material can enter the sampler is a constant when the speed of the sampling device through the stream remains constant. If this criterion is not met, and there is segregation of the particles in the process stream with respect to particle size or particle composition that arises due vibration or the manner of loading the material onto to the belt, the sample increments will be biased. The extent of the bias will depend on the extent of segregation and any failings of the design. If a sampling device can be shown to meet this first criterion of lack of bias, a practical test can be carried out to verify that it is indeed unbiased under circumstances of practical operation. It is important to verify that all the particles that are supposed to be collected into an increment are collected without any overflow of the sampling device and that particles that are not supposed to be collected are not collected; it can happen that even though the sampling device has a suitable geometry and motion, it imparts momentum by friction or impact to particles that should not be collected and these particles are collected into the increment. An optimal design for a sampling device will meet the first criterion on its geometry and its motion and will also have design features that minimise the momentum transfer to particles that are not part of the increment to be collected. A sampling device that operates at constant speed and meets the first criterion is said to be mechanically correct.

In its most simple form, the cross-belt sampler is a flat rectangular surface equipped with two parallel side plates to delimit the sample (see FIG. 1) and swings through the load of solids on the conveyor belt in a plane normal to the direction of travel of the belt. Such a sampler geometry is disclosed by Ford in U.S. Pat. No. 5,392,659. The solids trapped between the side plates and the rear plate of the sampler and the surface of the belt are accelerated in a direction normal their motion on the belt and are thrown off the side of the belt into a chute of suitable geometry (not shown). With the objective of sweeping off the belt any particles remaining within the path of the sampler head, there is often an adjustable wiper or scraper or brush fixed to the trailing edge of the sampler; a wiper is usually made of a flexible material and may be adjustable. The use of a brush at the trailing edge of a cross-belt sampler is described in van der Merwe, in U.S. Pat. No. 5,115,688.

Note that the profile of the belt must be closely controlled with special idlers to ensure that is a section of a cylinder in section normal to the direction of travel of the belt (as it is shown in FIG. 1) or that the design of the sampler is such that it effectively exerts a pressure on the belt as it moves over the belt so that the edges of the sampler remain in good contact with the belt, preventing particles that should be part of the sample increment from flowing under the edges of the sampler and being lost. Long considers this problem, U.S. Pat. No. 5,767,421. The technical descriptions provided herein assume that such shaping and/or support of the belt has been accomplished. If such constraint of the belt has not been accomplished, a cross-belt sampler cannot function in a technically useful manner.

In a more complex design, the two parallel plates delimiting the sample are set at an angle to the motion of the sampler head. The angle may be chosen so that the vector direction of the velocity of the solids at the surface of the belt relative to the cross-belt sampler is parallel to the plates. If the speed of the cross-belt sampler at its extreme radius is equal to the speed of the belt, the angle is set to 45 degrees. If the speed of the cross-belt sampler at the belt surface is $\sqrt{3}v_B$, where $v_B$ is the speed of the belt, the angle is 60 degrees. A sampler with angled side plates is displayed in FIG. 2. The inclination of the plates permits the solids to enter the sampler with a velocity relative to the moving sampler that is directed approximately parallel to the side plates. To maintain close contact with the belt, the side plates must have a partially elliptical shape where they contact the belt. This design with angled side plates is disclosed in van der Merwe, U.S. Pat. No. 5,115,688.

It is also known (see ISO 13909-2-2001 Hard coal and coke—Mechanical sampling—Part 2—Coal—Sampling from moving streams) to have a sample cutter of a geometry as shown in FIG. 1 which rotates on an axis as indicated in FIG. 1 but which is carried on a moveable trolley above the belt, the trolley being put into motion parallel to the motion of the belt before the sampling device contacts the belt or the solids on the belt. The trolley moves at the same speed as the belt. Such a sampler is capable of collecting the material between its parallel side plates and the swath of the device on the belt is at right angles to the motion of the belt.

The three embodiments of the cross-belt sampler described above constitute the state of the art in cross-belt sampler design.

The International Standards (for example, Australian Standard AS 4264.1-1995 and ISO 13909-2-2001 Hard coal and coke—Mechanical sampling—Part 2—Coal—Sampling from moving streams) that describe sampling devices and the cross-belt sampler in particular consider the cross-belt sampler to be a somewhat flawed device and it is generally believed that cross-belt samplers take biased samples. It is also relevant that Australian Standard AS 4264.1-1995 requires that the absolute speed of the sampler head at the surface of the belt exceed 1.5 times the belt speed. The Standard states that cross-belt samplers are not to be used for commercial purposes except where the device can be shown to be free of a defined level of bias that is acceptable under the particular circumstances of sampling.

The reason for the possible bias in the sample taken by the cross-belt sampler has not previously been explained. For some materials and applications, the inherent bias of the cross-belt sampler design, while it continues to exist, is not large enough to discourage or preclude the use of the machine. Even a poorly designed sampler will appear to be unbiased if it is used to sample an essentially homogeneous material. Because of the general failure by sampling technologists to understand why the conventional designs of cross-belt sampler are biased, the tolerance of bias at a level deemed insignificant in a given circumstance is condoned. Much of the testing for significant bias of the devices has been carried out in a manner that precludes the application of robust statistical method to the test results.

SUMMARY OF THE INVENTION

It can be shown mathematically that the current design of the cross-belt sampler as described above, except for the moving trolley type, is inherently biased due to a defect in its geometry. This defect in design has, to the present, escaped the notice of sampler designers, vendors and users.

The design principle for a cross-belt sampler disclosed herein corrects, or ameliorates, the faults in current designs and the new design can be shown to produce devices that are theoretically unbiased. These new geometrical rules for design of the cross-belt sampler have not been suggested previously and therefore the range of designs possible is entirely novel. The range of designs possible preferably accommodates a range of belt curvatures, widths of sampler openings and/or ratios of speed of the sampler head at the surface of the belt to the speed of the belt.

The accepted standard for the design of a so-called mechanically correct sampler is the cross-stream sampler. In its simplest form, a cross-stream sampler is a device having a rectangular opening which is moved in rectilinear motion through a falling stream of material. All parts of the falling stream can be intercepted at some point on the sampler path. This device diverts or collects the material falling through the opening of the device and this diverted or collected material forms the sample of the material or an increment of the final sample of the material.

For a sampling device to be unbiased, the geometry of the sample cutter head must be such that it moves through the stream of material to be sampled at a constant velocity and, on any two arbitrary particle trajectories within the flowing stream, the time interval between the passage of the leading edge of the cutter head and the passage of the trailing edge of the cutter head must be equal. Stated in another way, the time interval over which the flux of material through the plane of motion of the sample cutter edges is collected into the sampler cutter head must be constant, and independent of the position within the flowing stream considered. This requirement for constant time of influx into the sample cutter head can be referred to as the constant speed and sampling time criterion. Any device which does not satisfy this criterion can be said to take a biased sample or increment from the falling or flowing stream. When the design of the sampling device meets the constant speed and sampling time criterion, the sample increments taken will be unbiased and the sampler can be said to be mechanically correct as long as material that is not properly part of the sample or sample increment is not collected in addition to the material which should be collected.

The constant speed and sampling time criterion has never been applied to the cross-belt sampler design. Because existing cross-belt samplers as described above (except the moving trolley type) do not satisfy this criterion, they are all biased. In what follows, the moving trolley type cross-belt sampler is excluded from consideration.

The invention disclosed herein applies the constant speed and sampling time criterion design principle for the first time to the cross-belt sampler to arrive at a set of geometries for the cross-belt sampler cutter head that will provide theoretically unbiased samples. The most important difference in the geometry of the new cross-belt sampler design, compared to the conventional designs is that the leading edges of the cross-belt sampler cutter head are angled so as to meet on the axis of rotation of the sampler. This change of the edges of the cross-belt sampler cutter head from parallel to converging on the rotational axis makes the cross-belt sampler a correct and unbiased sampling device because it then satisfies the constant speed and sampling time criterion. All previous designs have used parallel cutter edges and, as a result, are biased. The extent of the bias will increase as the material on the belt becomes more highly segregated with respect to distance from the surface of the belt. Due to the shaking of the material on the belt as it moves across each idler and the tendency for larger particles to rill to the outside edge of the belt, such segregation is common.

The simplest form of the new design involves a cross-belt sampler cutter head that has an opening that is a segment or truncated segment of a circle when viewed in a plane perpendicular to the axis of rotation of the cutter head. The truncation of the segment must be such that only radially oriented cutter edges pass through the flowing stream. The axis of rotation of the cutter head must be parallel to the motion of the belt. A cutter head of this design must have a volume that is adequate to hold the volume of material that flows into it while it passes through the material flow on the belt and the entirety of the material collected must be ejected into a suitable collection chute at the side of the belt.

A further preferred design objective for a cross-belt sampler involves minimising the momentum transferred to material on the belt that is not collected in the interior of the sampler. It is possible that material that gains momentum from the passage of the cutter head through the load of material on the belt will be directed into the chute at the side of the belt, causing adulteration of the sample increment. A simple design for a cross-belt sampler that meets the constant speed and sampling time criterion might have planar side plates oriented so that lines coincident with the leading edges of those side plates meet at the centre of rotation. However, this simple design suffers from the defect that it may impart undesirable momentum to the solids that flow past the sampler head on the outside of the side plates.

To understand the momentum transfer problem, it is necessary to make a technical analysis of the relative motion between the cutter head and the solids conveyed on the belt. If the speed of the cutter head at the belt surface is $v_H$ and the belt speed is $V_B$, the cosine of the angle between the axis of rotation and the vector velocity of the solids relative to the cutter head at a point on the cutter head at a distance r from the axis of rotation can be shown to be:

$$\cos\phi = \frac{v_B}{\sqrt{v_B^2 + \left(\frac{rv_H}{R}\right)^2}} \qquad 1$$

where R is the distance from the axis of rotation to the belt surface. In a circumstance that $v_H=\sqrt{3}v_B$, the angle is $\phi=60$ degrees for r=R. For r=0.6R, $\phi$=46.1 degrees. Equation 1 shows that the angle of entry of the solids into the cutter head changes with the radial distance from the centre of rotation.

In a case wherein the motion of the solids relative to the cutter head is not strictly parallel to the sides of the cutter head, at every point on the exterior surface of the head, the motion of the cutter head will impart a component of momentum to the solids outside the sample cutter head. This momentum component will be in the direction of motion of the cutter head and will impart an additional velocity component to particles that did not enter into the cutter head. This velocity component will propel the particles towards the collection chute at the side of the belt. If sufficiently large, it will cause the collection into the chute of particles that are not properly a component of the correctly intercepted sample or sample increment. It is therefore desirable, especially for heavily loaded belts, to take the entry angle into account and provide a sampler head for which particle motion outside the sampler is always parallel to the side of the cutter.

To minimise the acceleration of solids that are not properly part of the sample or sample increment, the side plates of the cutter head must be everywhere parallel to the velocity vector of the solids relative to the cutter head. Using Equation 1, a geometry for the cutter head substantially as shown in the drawings FIG. 3 (front view), FIG. 4 (rear view) and FIG. 5 (top view) is required. To determine the optimal shape of the cutter head in general circumstances, it is necessary to consider a series of planes parallel to the axis of rotation of the cutter head and perpendicular to a line bisecting the opening of the cutter head. Within one such plane, Equation 1 can be used to construct a differential equation the solution to which gives the locus of the intersection of the outer surface of the side plate with the plane considered. This equation can be solved explicitly to provide the data needed to manufacture the device. The cutter head geometry of FIG. 3 has been formulated on such a basis and will lead to minimal acceleration of particles that should not be part of the sample increment and it is clear from the Figure that the geometry does not pose any major fabrication problems. As the design volume of the cutter head increases, the curvature of the loci increase; in the illustration provided, the loci curvatures are low and not particularly apparent.

Since the cross-belt sampler cutter head must contain the solids to be removed from the belt, the interior volume of the cutter head must be matched to the circumstances of its application. However, as the solids must discharge cleanly from the cutter head, the interior of the cutter head should have no corners with acute angles into which solids may pack. To reduce the probability of retention of solids, the rear of the cutter head can be truncated in a manner that avoids interior corners with acute interior angles. The required overall size of the cutter head is related to the mass flow on the belt, the particle size of the solids, the practical range of curvature of the belt and the ratio of the head speed to belt speed. The required cutter head volume must be considered for each application and the cutter head designed according to the novel principles disclosed herein that lead to mechanically correct and optimal design. The volume of the cutter head should exceed the volume of the increment to be collected by perhaps 50%.

In summary, two new design principles for the cross-belt sampler are disclosed herein. First, the rule that the projection of the edges of the sample cutter onto a plane normal to the axis of rotation of the sample cutter must form a segment of a circle or a truncated segment of a circle ensures that the theoretical sample collected is unbiased. When the cutter head moves at constant speed, the cutter design will meet the constant speed and sampling time criterion. Second, the application of a mathematical relationship, Equation 1, which describes the vector velocity of the solids relative to the sample cutter, permits, under the disclosure herein, the construction of a sample cutter head of a practical geometry that will impart minimal momentum to those solids on the belt which are outside the sample cutter. This latter feature is important in minimising the probability that material that should not be collected into the sample or sample increment is not in fact collected. The first design rule provides the critical element of the sample cutter geometry that makes the cutter head theoretically unbiased when it is operated at constant speed. The second design rule optimises the practical design of the sample cutter head. Used together, the design rules provide for an optimal sampler cutter head geometry.

The design rules disclosed herein can be applied to create practical geometries for a range of subtended angles of the front opening of the sample cutter head and a range of distances between the axis of rotation and the belt surface. Similarly, the overall volume of the sample cutter head can be increased or decreased as needed to accommodate the volume of material to be swept off the belt.

DETAILED DESCRIPTION OF THE DRAWINGS

To enable the invention to be fully understood, preferred embodiments will now be described with reference to the accompanying drawings in which.

DETAILED DESCRIPTION OF THE PREFERRED EMBODIMENTS

Figure 1:
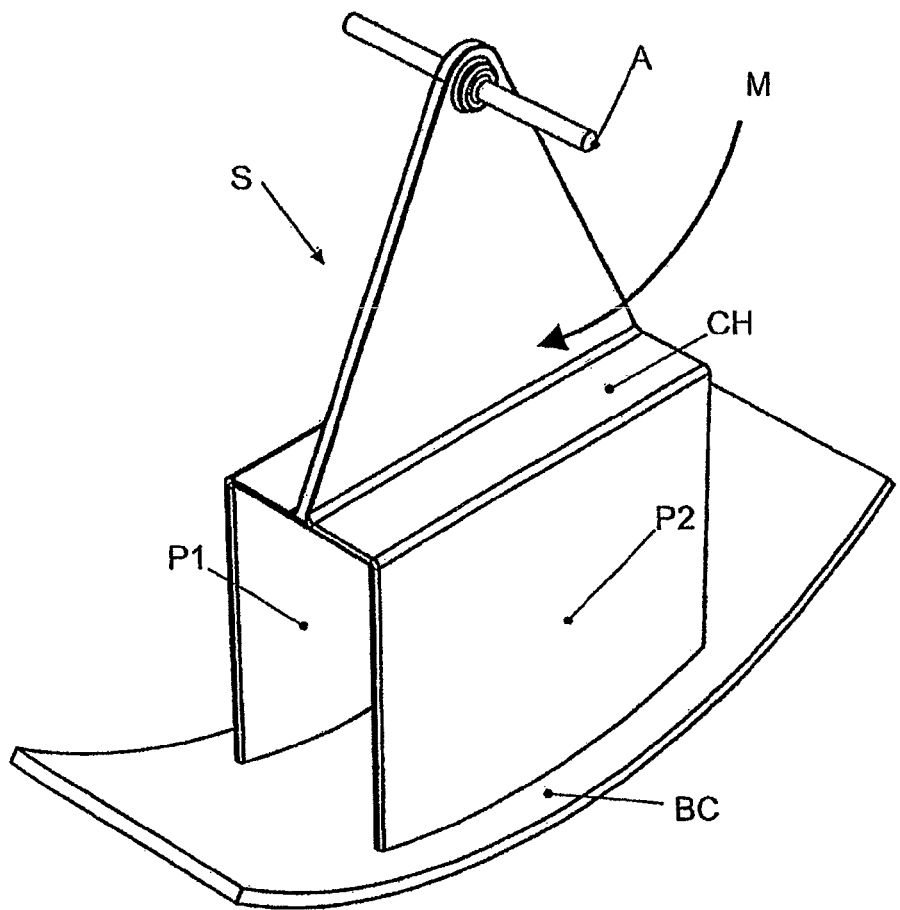
FIGS. 1 and 2 are respective isometric views of examples of the PRIOR ART cross-belt samplers hereinbefore described.
Figure 2:
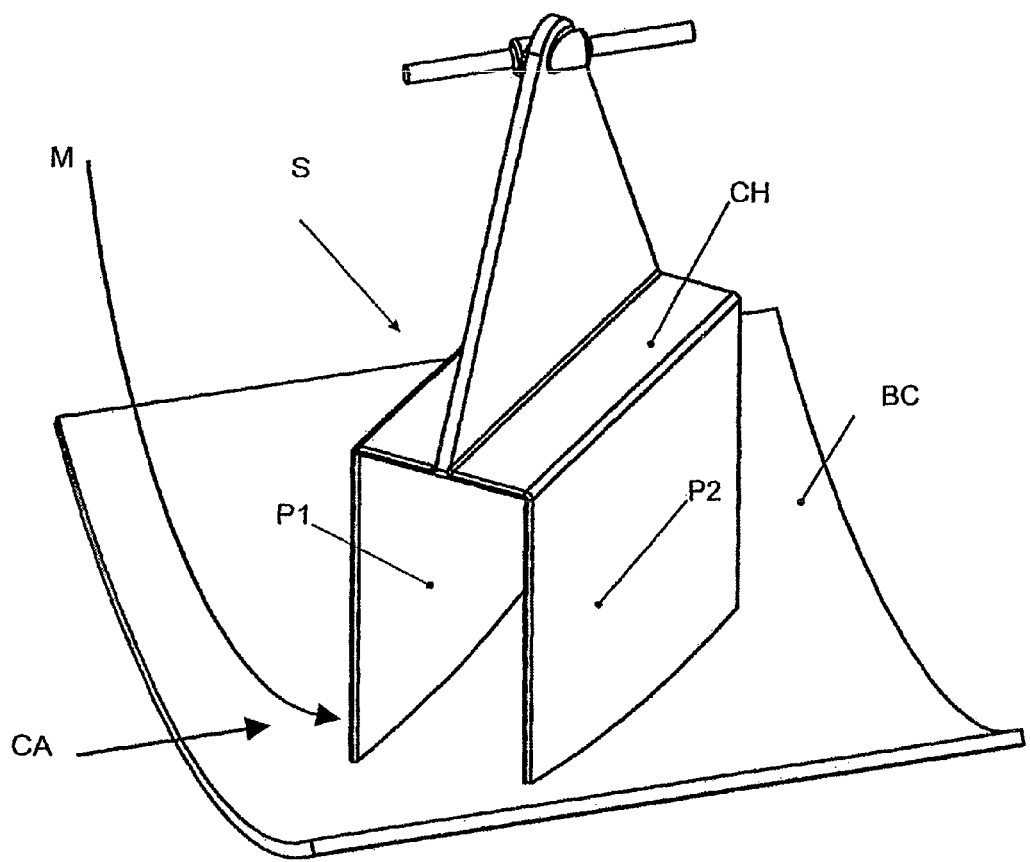

As hereinbefore described, FIGS. 1 and 2 illustrate examples of PRIOR ART cross-belt samplers S operating in conjunction with a belt conveyor BC.

The cutter head CH has a pair of parallel side plates P1, P2 which delimit the sample (not shown) taken from material being conveyed on the belt conveyor BC.

The sampler S in FIG. 1 has its axis of rotation A parallel to the central axis of the belt conveyor BC and the side plates P1, P2 are parallel to the motion M of the cutter head CH; while the sampler S in FIG. 2 has its side plates P1, P2 at an angle, eg., 45° or 60° to the motion M of the cutter head CH relative to the belt conveyor BC.

Figure 3:
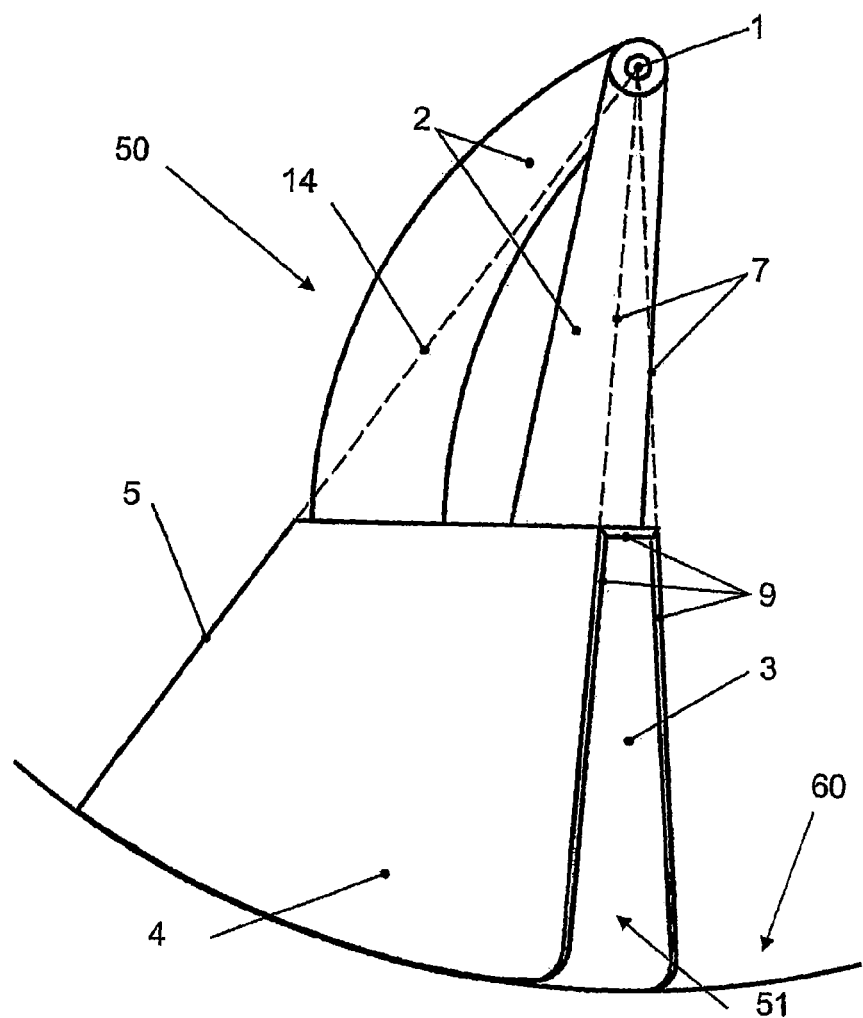
FIG. 3 is a side elevational view of the cutter head of a cross-belt sampler in accordance with the present invention.

FIG. 3 is a side elevational view of the cutter head 50, of the present invention, in a position such that the axis of rotation 1 of the device is perpendicular to the plane of the drawing. The cutter head is attached to the shaft 1 by suitable arms 2 fixed to the shaft 1 and to the body of the cutter head 50. The sampler opening 51 of the cutter head 50, into which the sample increment is collected, is defined by cutting edges 9 of side plates 3 and 4 and top plate 8 and the belt surface 10. Side plates 3 and 4 are curved plates shaped according to the design principles described above and meeting the constant sampling time criterion. The bottom of the cutter head 50 where it contacts the belt 60 is open. The rear of the cutter head 50 is formed by plates 5 and 6. While rear plate 5 is oriented parallel to a plane passing through the axis of rotation with the objective of assisting a full discharge of the solids from the sample cutter, truncation plate 6 truncates the sampler cutter head volume so as to eliminate what would otherwise be a corner with acute angles into which solids might compact.

Figure 4:
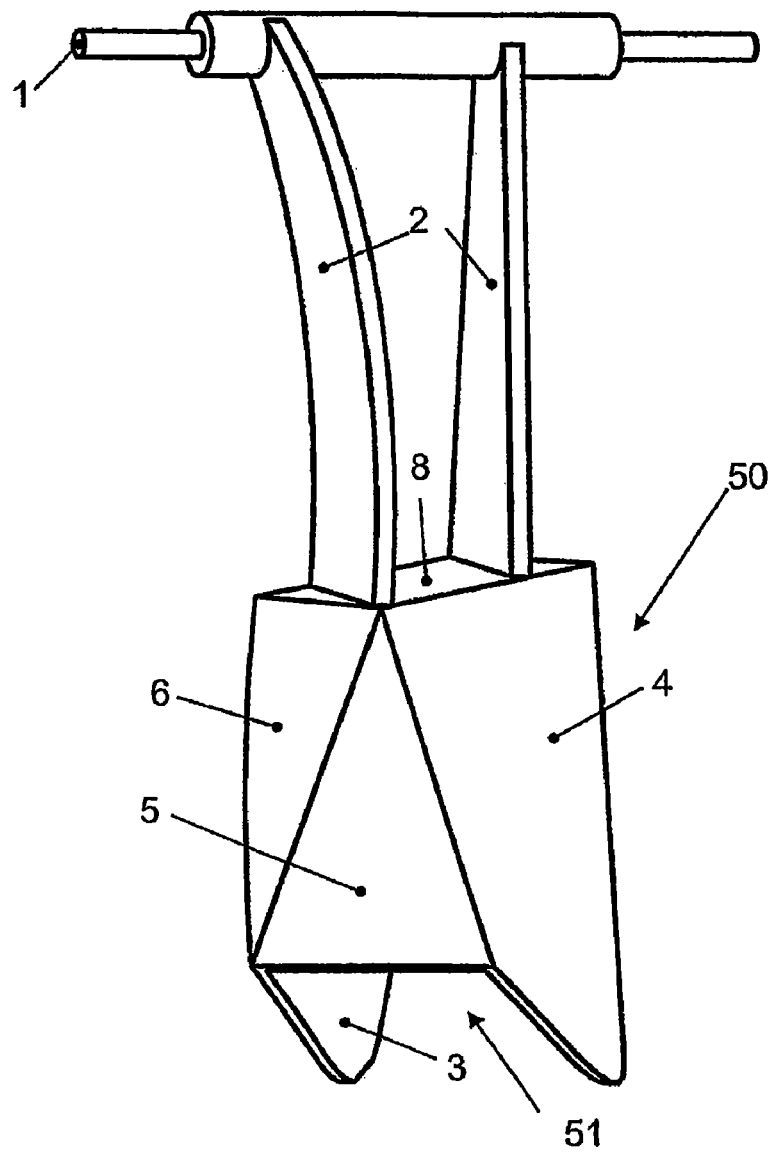
FIG. 4 is a rear elevational view thereof.
Figure 5:
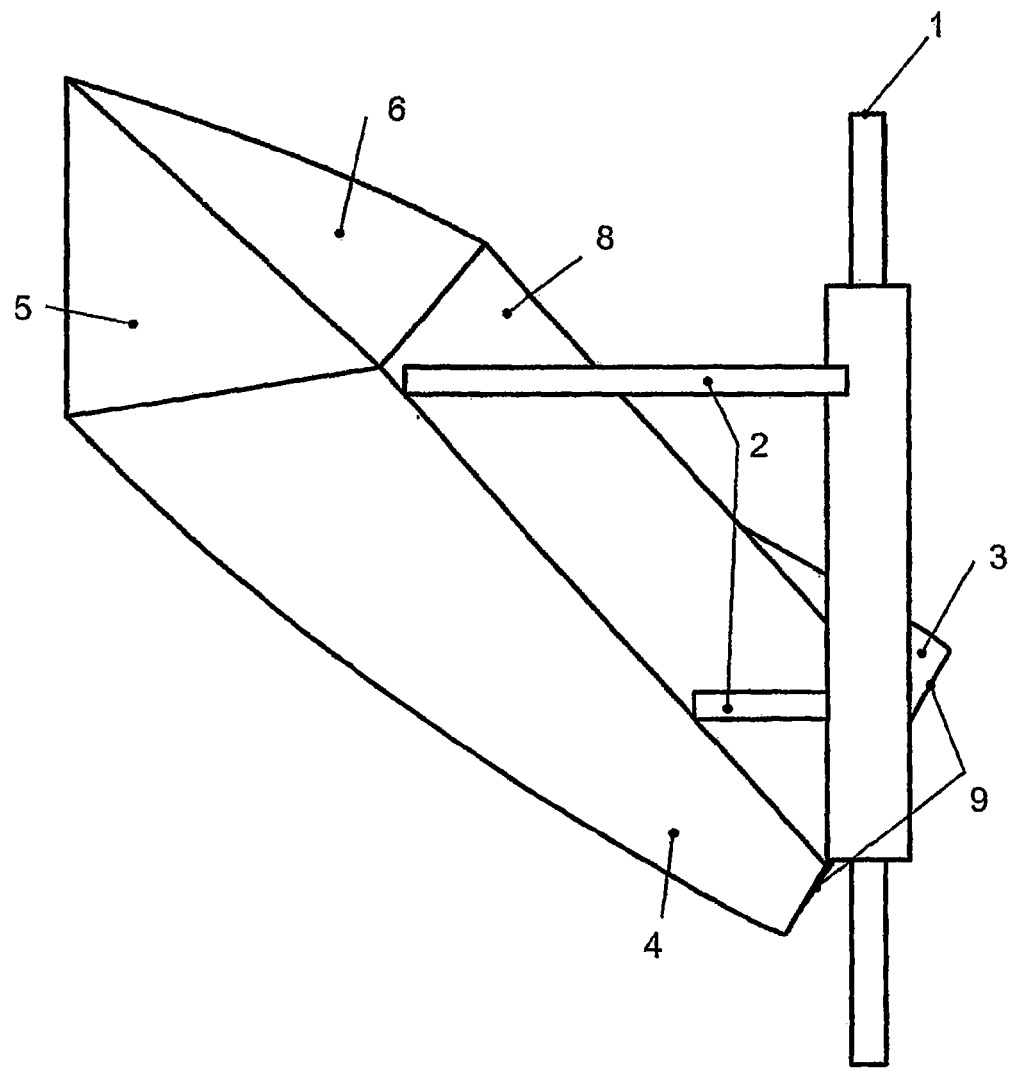
FIG. 5 is a top plan view thereof.

FIG. 4 provides a rear view of the cutter head 50 and FIG. 5 provides a top view thereof. The top view is intended to provide an impression of how the shape of the cutter head 50 changes with distance from the axis of rotation 1 in order to ensure that the motion of the solids past the exterior surface of the cutter head 50 is everywhere parallel to the surface.

Figure 6:
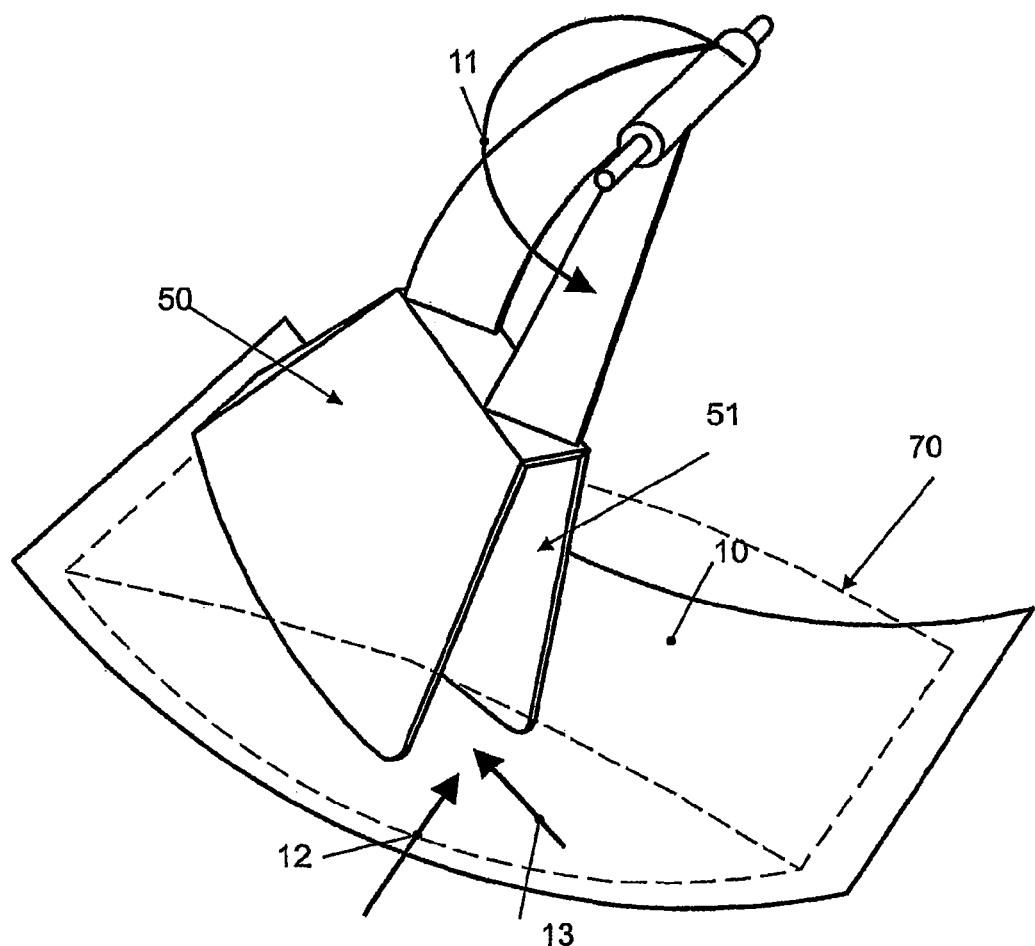
FIG. 6 is an isometric view thereof.

FIG. 6 shows a segment of the conveyor belt surface 10 over which the cutter head 50 must move and the sense of rotation 11 of the cutter head 50. The vector 12 shows the motion of the belt 60. Vector 13 indicates direction of entry of the solids 70, shown figuratively as an outline in dashed lines, into the cutter head 50, relative to the cutter head 50.

As stated above, the belt 60 must be contoured or shaped to a partially cylindrical shape so that the cutter head 50 remains in close contact with the belt 60 as it moves over the belt surface 10. Similarly, this contact must be sufficiently positive to ensure that the cutter head 50 sweeps the material 70 that is properly part of the sample increment from the belt 60 without leaving particles behind.

In reference to FIG. 3, it is necessary that the projection of the cutter edges 9 onto a plane normal to the axis of rotation 1 follow lines 7 that meet at the axis of rotation 1. Note also in FIG. 3 that the rear plate 5 of the cutter head 50 is arranged so that its surface falls in a plane 14 that passes through the axis of rotation 1. While other orientations of the rear plate 5 may be used, or a curved surface provided inside the cutter head 50, the orientation shown will ensure that the centrifugal force on the solids inside the cutter head 50 acts parallel to the rear plate 5, leading to a maximum shearing force between the solids and the rear plate 5 which will assist discharge of the solids from the interior of the cutter head 50 once it loses contact with the belt surface 10.

Figure 7:
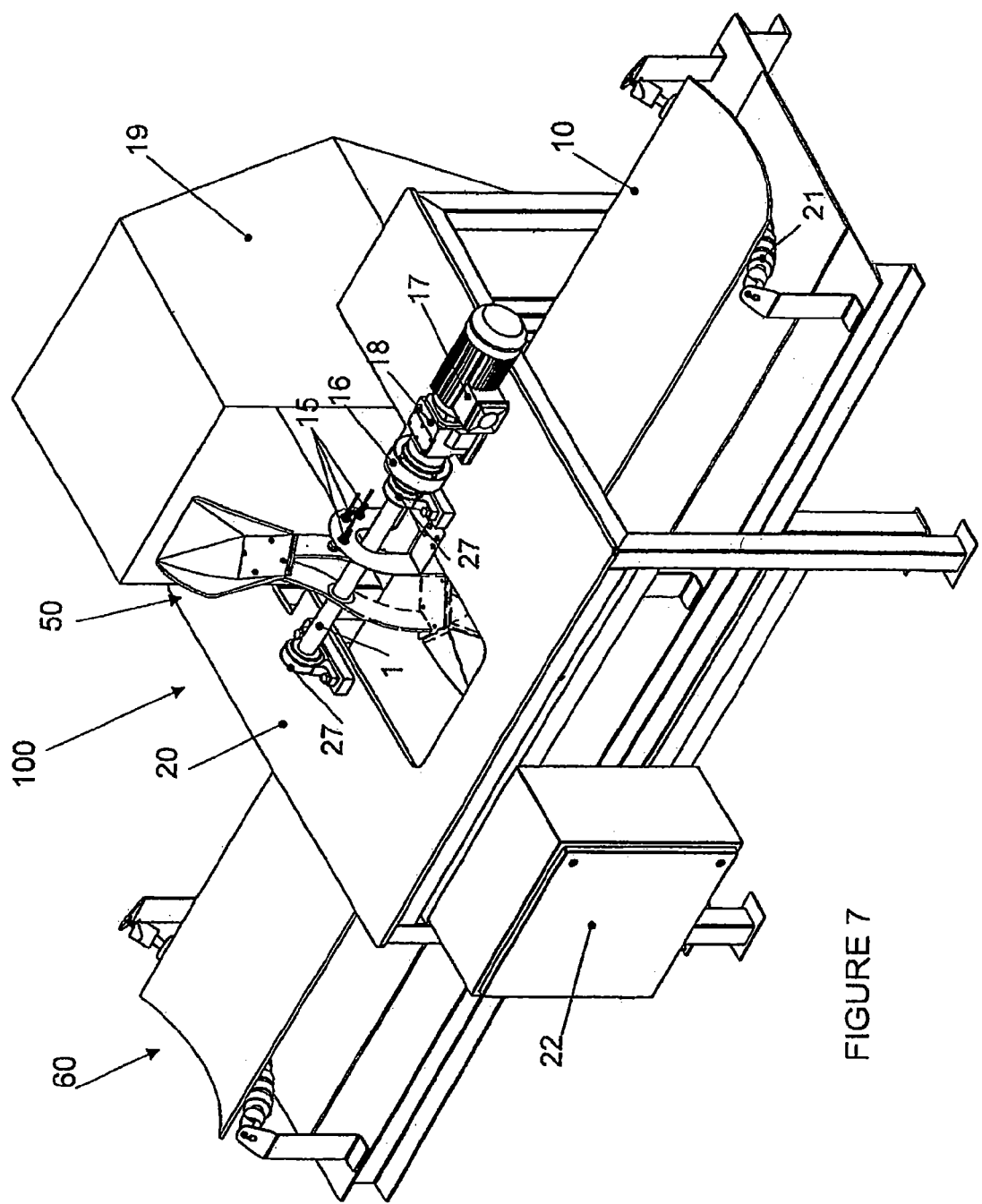
FIG. 7 is an isometric view of the cross-belt sampler of the present invention and of an adjacent portion of a belt conveyor.
Figure 11:
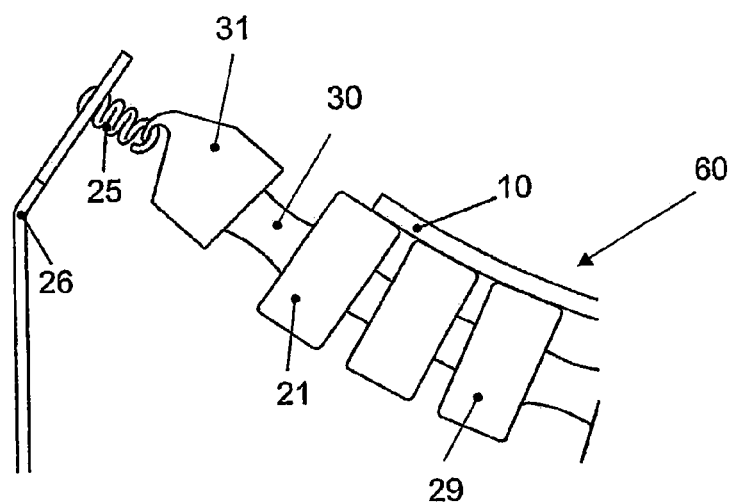
FIG. 11 is a side elevational view of the spring-mounted idlers for the belt conveyor.

The cutter head 50 is driven in the same manner as existing cross-belt samplers. FIG. 7 shows and overall assembly of the cross-belt sampler 100, showing a support frame 20 upon which the cutter head 50 rotates on the shaft 1, supported by bearings 27, and driven by an electric motor 17 coupled to the shaft through a gearbox 18 and a coupling 16. The frame 20 stands on the general structure of the conveyor system which supports the belt 60 which, in the vicinity of the cutter head 50, is supported on flexible idlers 21. These idlers 21 are constructed by forming rubber rollers 29 around a steel cable 30 which rotates in bearings in terminal hook-pieces 31 at each end of the unit. These types of conveyor support are well-known and have the advantage of permitting more deformation of the belt profile than other types of conveyor idlers. In the case of the present invention, the idlers 21 are supported by springs 25 connecting the hook-pieces 31 to the conventional conveyor support point 26 as shown in FIG. 11. The springs 25 serve to protect the conveyor idler bearings from excessive axial loads when the belt profile is deformed by the passage of the cutter head 50 across the belt 60.

FIG. 7 shows the cutter head 50 in two positions: the parked position above the belt 60 (solid lines) and in a position during its passage through the material on the belt 60 (dotted lines).

Figure 8:
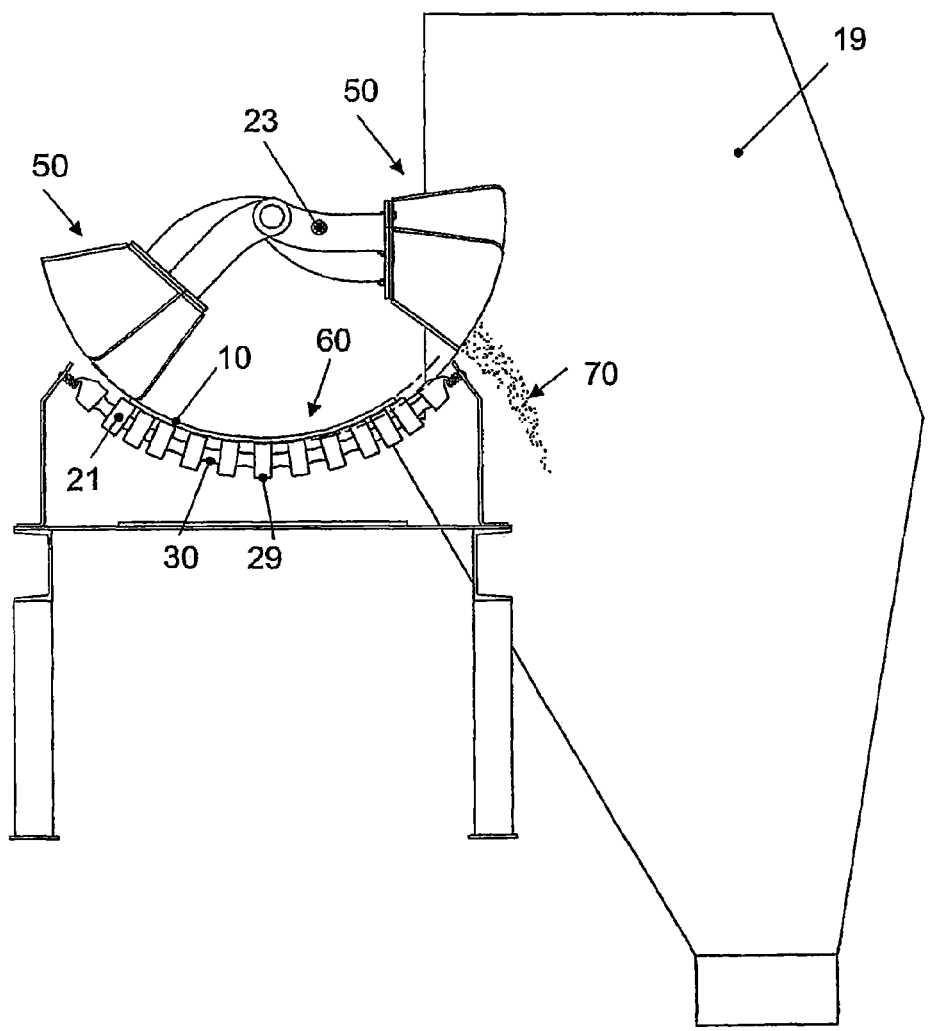
FIG. 8 is a side elevational view thereof (parts being omitted for clarity) showing the cutter head in alternative positions during the sampling cycle.

The motion of the sampler cutter head 50 is governed by a controller 22 which contains various electrical circuitry and a variable speed motor drive (also known as an inverter drive) of conventional design. FIG. 8 shows the cutter head 50 as it first contacts the surface 10 of the conveyor belt 60 and just as it has left the surface 10 of the conveyor belt 60 and is discharging the solids 70 collected in its passage into the collection chute 19.

Figure 10:
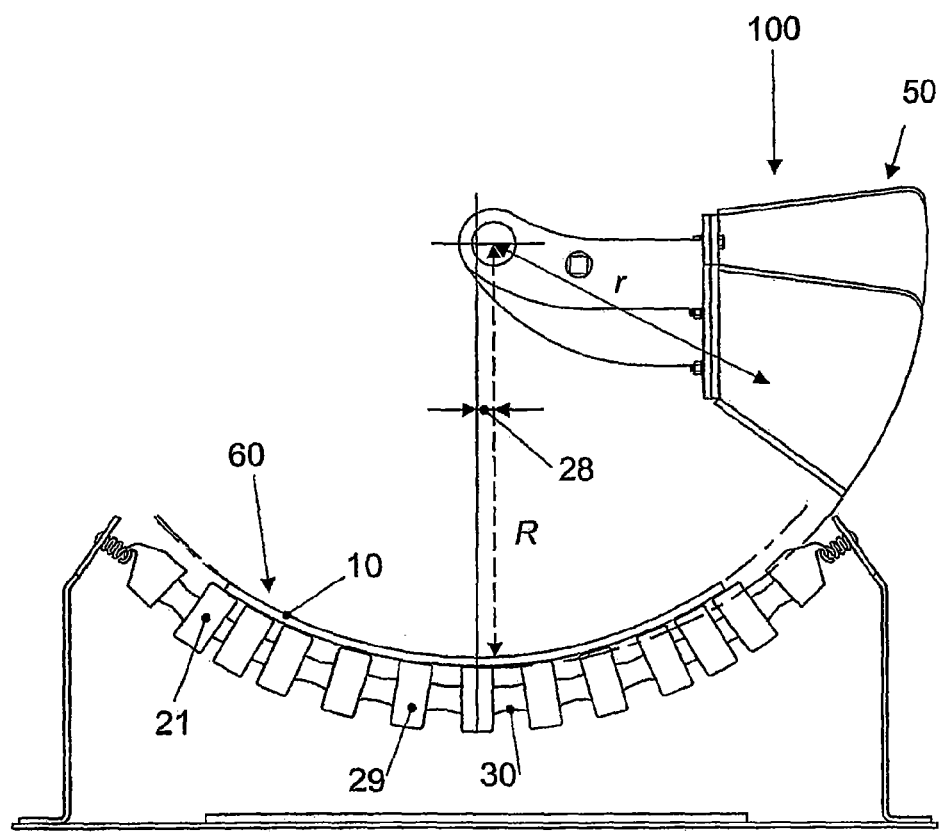
FIG. 10 is a side elevational view illustrating the offset of the axis of rotation of the cutter head relative to the central axis of the belt conveyor.

It is critical that the solids 70 collected into the interior of the cutter head 50 as it moves across the belt 60 remain inside the cutter head 50 and not leak out under the trailing edge of the cutter formed by the side plates 4 and the rear plate 4. To ensure that the cutter head 50 remains firmly pressed against the belt 60, the axis of rotation 1 of the cutter head 50 is slightly offset by a distance 28 from the centreline of the belt 60 as shown in FIG. 10. This offset causes the cutter head 50 to push down on the surface 10 of the belt 60 progressively displacing it from its original semicircular contour as the cutter head 50 progresses across the belt 60. This deformation is catered for by the means of support of the belt 60 locally by the spring mounted flexible idlers 21.

Figure 12:
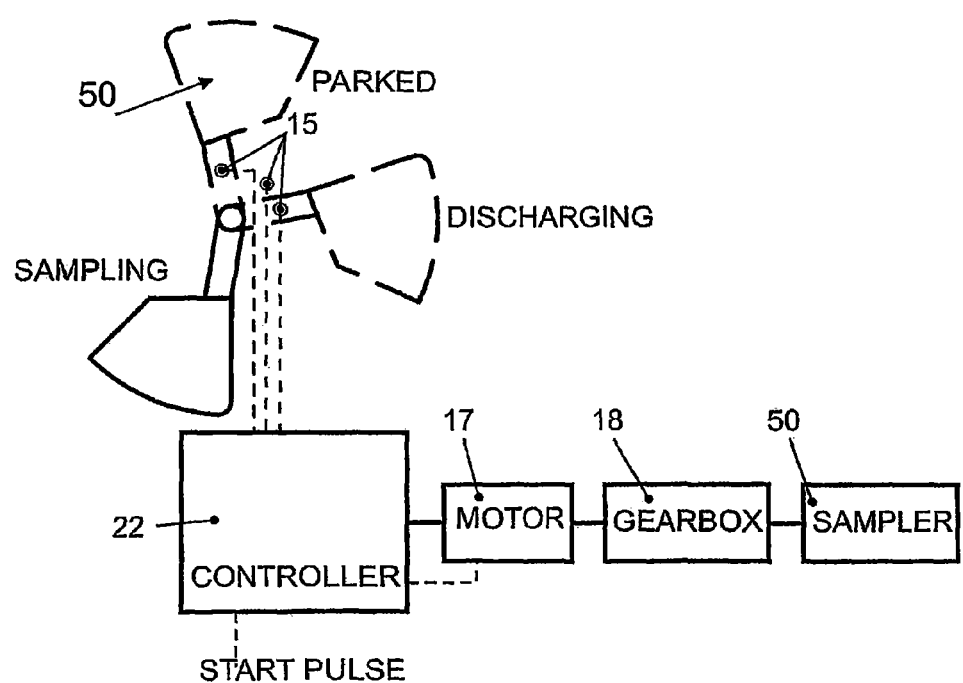
FIG. 12 is a schematic diagram of the control system for the cross-belt sampler.

The control system is shown schematically in FIG. 12. The motion of the cutter head 50 is initiated by a start pulse from a remote device or a local switch. This pulse acts on the control circuitry in controller 22 to start the motor 17 which accelerates from motionless to the required speed to drive the cutter head 50 at the desired speed, which is directly related to the belt speed. The time over which the acceleration takes place is calculated to ensure that the cutter head 50 accelerates over approximately 120 degrees of motion from its rest position above the belt 60. The motor 17 then runs at constant speed until the arm 2 of the cutter head 50 passes the first of three proximity switches 15. This switch initiates the deceleration of the cutter head 50. The time for deceleration is calculated to bring the cutter head 50 to rest in the position from which it started, in which position it activates the third of the three proximity switches 15. The second of the three proximity switches 15 forms part of a failsafe stopping system, which will initiate deceleration of the cutter head in the event that the first proximity switch 15 fails to operate. The circuitry that is used to ensure the motion of the sampling head just described is conventional.

Figure 9:
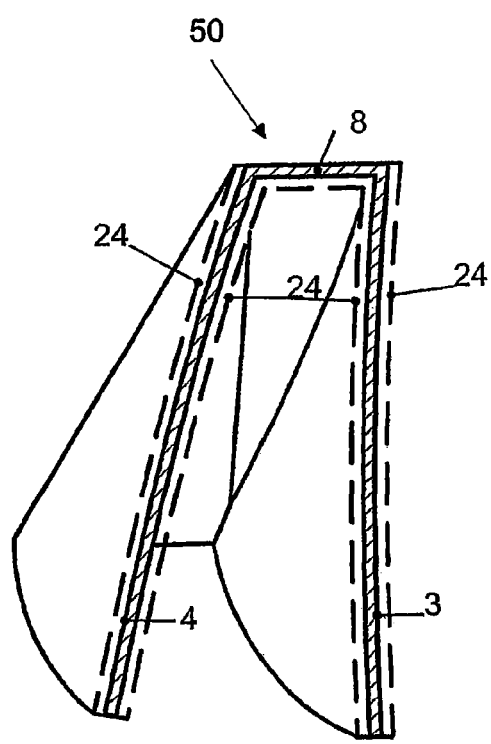
FIG. 9 illustrates the construction of the cutter head.

The cutter head 50 may be constructed of a variety of materials that provide sufficient rigidity to retain the shape of the cutter head 50 as it moves through the load of material 70 on the belt 60. The material of construction may be chosen to provide resistance to wear by the material 70 to be sampled and due to impact between the material 70 being sampled and the cutter head 50. The material and mode of construction of the cutter head 50 may be chosen to reduce the moment of inertia of the cutter head 50 about the axis of rotation 1 as this reduction reduces the demand for mechanical strength in the mounting frame 20 and for the power needed to accelerate and decelerate the cutter head 50 during its motion. In the simplest case, where the material 70 to be sampled is of relatively low density and not abrasive, common metal construction may prove effective. In more extreme duties where the material sampled 70 is dense and substantially more abrasive, and there is a desire to reduce the moment of inertia of the cutter head 50, the cutter head 50 may be constructed of composite materials of high wear and impact resistance formed over an internal skeleton of suitably rigid design as shown in FIG. 9. The metal skeleton formed by side plates 3 and 4, the rear plate 5, and the truncating plate 6 (not shown in FIG. 9) and the top plate 8 of the cutter head 50 can be coated with wear-resistant material 24 on both surfaces of the plates 3 to 6 and on the underside of the top plate 8.

In a practical application of the cutter head, the minimum spacing between the side plates 3 and 4 is preferably not less than three (3) times the top size of the particles of the material being sampled; and the volume of the cutter head is preferably at least 125%, more preferably at least 150% of the volume of the sample increment.

Furthermore, the lower edges of the side plates 3 and 4 are preferably drawn to a cylindrical shape when viewed in a plane perpendicular to the axis of rotation; but that shape may be varied to suit the particular application.

Various changes and modifications may be made to the preferred embodiments hereinbefore described and illustrated without departing from the present invention.

The invention claimed is:

1. A cutter head for a cross-belt sampler for the sampling of a flowing stream of material on a belt conveyor, the cutter head being of a type having a pair of side plates interconnected by a rear plate and top plate, leading edges of the side plates defining a sampling opening, and the cutter head being operable for rotation through a sampling cycle about an axis of rotation parallel to a longitudinal axis of the belt conveyor, wherein:
the leading edges of the side plates are inclined and, when orthographically projected into a plane perpendicular to the motion of the solids on the belt, fall on two straight lines which meet at the axis of rotation of the cutter head.

2. A cutter head as claimed in claim 1 wherein:
the sampling opening defines a segment or truncated segment of a circle when viewed in a plane perpendicular to the axis of rotation of the cutter head.

3. A cutter head as claimed in claim 2, wherein:
when the sampling opening defines a truncated segment of a circle, only radially oriented leading edges of the side plates pass through the flowing stream of the material to be sampled on the belt conveyor.

4. A cutter head as claimed in claim 1, wherein:
the rear plate lies on a plane passing through the axis of rotation.

5. A cutter head as claimed in claim 1, and further including:
a truncating plate interconnecting the rear plate, top plate and the respective side plates in the downstream direction of the flow of the material along the belt conveyor, the truncating plate eliminating a corner with acute angles in the cutter head into which the materials might pack.

6. A cutter head as claimed in claim 1, wherein:
in use, the exterior surfaces of the side plates are shaped so as to be everywhere parallel to the velocity vector of the solids on the conveyor relative to the cutter head, when the cutter head moves at a constant angular velocity.

7. A cutter head as claimed in claim 1, wherein:
a minimum distance between the side plates is not less than three times a top size of particles of the material being sampled.

8. A material sampler comprising a cutter head as claimed in claim 7 and a receiving chute wherein:
the cutter head deposits samples of the material to a the receiving unit.

9. A cutter head as claimed in claim 1, wherein:
the volume of the cutter head is at least 150% of the volume of a sample increment removed from the material during a sampling cycle.

10. A cutter head as claimed in claim 1, wherein:
lower edges of the side plates are drawn to a cylindrical shape when viewed in a plane perpendicular to the axis of rotation.

11. A cutter head as claimed in claim 1, wherein:
at least one surface of the side plates, rear plate, truncating plate and/or top plate are coated with wear-resistant material.

12. A cross-belt sampler for material conveyed on a belt conveyor including:
a drive shaft defining an axis of rotation parallel to a longitudinal axis of belt conveyor;
a cutter head as claimed in claim 1;
at least one arm connecting the cutter head to the drive shaft; and
drive means connected to the drive shaft and operable to move the cutting head at a constant angular velocity as it passes through a flow of material to be sampled, being conveyed on the belt conveyor.

13. A sampler as claimed in claim 12, wherein:
if the speed of the cutter head at a surface of the conveyor belt is $v_H$, and the speed of the belt conveyor is $v_B$, the cosine of the angle $\phi$ between the axis of rotation and a vector velocity of the material relative to the cutter head at any point on the cutter head at a distance r from the axis of rotation is given by the equation:

$$\cos\varphi = \frac{v_B}{\sqrt{v_B^2 + \left(\frac{rv_H}{R}\right)^2}}$$

where:

R=the distance of the axis of rotation to the surface of the belt conveyor.

14. A sampler as claimed in claim 12; wherein the axis of rotation is offset from the longitudinal axis of the belt conveyor to maintain the cutter head in contact with the belt conveyor as the cutter head progresses across the belt conveyor.

15. The sampler as claimed in claim 12 wherein:
the motion of the cutter head is governed by a controller connected to the drive means; and
the drive means includes a variable speed motor drive or inverter drive.

16. A materials sampling assembly including:
a belt conveyor; and
a sampler as claimed in claim 12 adjacent to the belt conveyor and operable to take samplers from a flow of material on the belt conveyor, travelling past the sampler.

17. An assembly as claimed in claim 16, wherein:
the belt conveyor has a belt supported with a variable curvature by a plurality of idlers at spaced distances along the belt conveyor; and
each idler has a plurality of spaced rollers on a cable, the ends of the cable being journalled in bearings connected to a support frame by respective springs.

* * * * *